United States Patent
Yalçinkaya et al.

(10) Patent No.: US 10,492,683 B2
(45) Date of Patent: Dec. 3, 2019

(54) SPLIT-RING RESONATOR-BASED STRAIN SENSOR ON FLEXIBLE SUBSTRATES FOR GLAUCOMA DETECTION

(71) Applicant: Bogazici Universitesi, Istanbul (TR)

(72) Inventors: Arda D. Yalçinkaya, Istanbul (TR);
Günhan Dündar, Istanbul (TR);
Hamdi Torun, Istanbul (TR)

(73) Assignee: BOGAZICI UNIVERSITESI, Istanbul (TR)

( * ) Notice: Subject to any disclaimer, the term of this patent is extended or adjusted under 35 U.S.C. 154(b) by 93 days.

(21) Appl. No.: 15/674,588

(22) Filed: Aug. 11, 2017

(65) Prior Publication Data
US 2018/0042479 A1    Feb. 15, 2018

Related U.S. Application Data

(60) Provisional application No. 62/374,023, filed on Aug. 12, 2016.

(51) Int. Cl.
*A61B 3/16* (2006.01)
*A61B 5/00* (2006.01)

(52) U.S. Cl.
CPC .............. *A61B 3/16* (2013.01); *A61B 5/6821* (2013.01); *A61B 2562/0247* (2013.01); *A61B 2562/0261* (2013.01); *A61B 2562/12* (2013.01)

(58) Field of Classification Search
CPC .............................................. A61B 2562/0247
See application file for complete search history.

(56) References Cited

U.S. PATENT DOCUMENTS

2017/0284968 A1\* 10/2017 Blumberg, Jr. ........ G01N 29/02

OTHER PUBLICATIONS

Chen et al. Microfabricated Implantable Parylene-Based Wireless Passive Intraocular Pressure Sensors. Journal of Microelectrochemical Systems, vol. 17, No. 6, Dec. 2008. p. 1342-1351 (Year: 2008).\*
T. Nagayama, M. Ruiz-Sandoval, B.F. Spencer, Jr.; K.A. Mechitov, G. Agha, "Wireless Strain Sensor Development for Civil Infrastructure",Trans. of the Society of Instrument and Control Engineers, vol. E-3, No. 1, 104/109 (2004).
R. Melik, N. K. Pekgoz, E. Unal, C. Puttlitz, and H. V. Demir, "Bio Implantable passive on-chip RF-MEMS strain sensing resonators for orthopaedic applications," J. Micromech. Microeng. 18(11), 115017 (2008).

(Continued)

*Primary Examiner* — Christian Jang
(74) *Attorney, Agent, or Firm* — Gokalp Bayramoglu

(57) ABSTRACT

The invention relates a split-ring resonator-based strain sensor on flexible substrates for glaucoma detection. The purpose of this invention is to provide a sensor which is electrically passive, wireless and low cost to measure intraocular pressure. It measures intraocular pressure by placing a microwave resonator on top of contact lenses. The sensor that is a metallic ring can be placed on a contact lens using standard methods of metal deposition (sputtering, evaporation, etc.) using a shadow mask. The sensor on the lens does not require any electrical signal to operate and are interrogated by external antennas that can be located away from the contact lens. This is very advantageous to define flexible strain sensors that are required for applications as glaucoma detection.

9 Claims, 7 Drawing Sheets

(56) References Cited

OTHER PUBLICATIONS

Rajni, A. Kaur, A. Marwaha, "Crack Detection on Metal Surfaces with an Array of Complementary Split Ring Resonators", International Journal of Computer Applications (0975-8887) vol. 119—No. 10, Jun. 2015.

"Five Common Glaucoma Tests", glaucoma.org, Glaucoma Research Foundation, Apr. 22, 2013.

B.K. Pierscionek, M. Asejczyk-Widlicka, R.A. Schachar, "The effect of changing incraocular pressure on the corneal and scleral curvatures in the fresh porcine eye", Br J Ophthalmol 2007;91:801-803. doi: 10.1136/bjo.2006.110221.

M. Leonardi, P. Leuenberger, D. Bertrand, A. Bertsch, P. Renaud, "First Steps toward Noninvasive Intraocular Pressure Monitoring with a Sensing Contact Lens", Invest. Ophthalmol. Vis. Sci., 45(9), 3113 (2004).

D. Piso, P. Veiga-Crespo, E. Vecino, "Modern Monitoring Intraocular Pressure Sensing Devices Based on Application Specific Integrated Circuits", Journal of Biomaterials and Nanobiotechnology, 2012, 3, 301-309.

* cited by examiner

SPLIT-RING RESONATOR-BASED STRAIN SENSOR ON FLEXIBLE SUBSTRATES FOR GLAUCOMA DETECTION

TECHNICAL FIELD

This invention relates to sensors, more specifically, relates to a split-ring resonator-based strain sensor on flexible substrates for glaucoma detection.

BACKGROUND

Wireless strain measurement attracts attention of many researchers and finds application in numerous fields when it comes to material characterization. In civil engineering, the sensors of the sort are used to ensure maintenance in infrastructure, by measuring the strain on the structure and take precaution in case of any abnormal strain (T. Nagayama, M. Ruiz-Sandoval, B. F. Spencer Jr., K. A. Mechitov, G. Agha, "Wireless Strain Sensor Development for Civil Infrastructure", Trans. of the Society of Instrument and Control Engineers, Vol. E-3, No. 1, 104/109 (2004)). In biomedical engineering, these sensors are utilized by observation of the healing process of a fractured bone (R. Melik, N. K. Pekgoz, E. Unal, C. Puttlitz, and H. V. Demir, "Bio Implantable passive on-chip RF-MEMS strain sensing resonators for orthopaedic applications," J. Micromech. Microeng. 18(11), 115017 (2008)). Moreover, in aerospace industry, wireless strain measurement comes into prominence in crack or abnormal strain detection on metal surfaces (Rajni, A. Kaur, A. Marwaha, "Crack Detection on Metal Surfaces with an Array of Complementary Split Ring Resonators", International Journal of Computer Applications (0975-8887) Volume 119-No. 10, June 2015). SRR-based sensors have been demonstrated for wireless strain measurement previously. The resonant frequency of the device strongly depends on the geometry of the ring and any deviation in geometry due to external strain applied to the device results in change in resonant frequency of the resonator. This enables strain measurement through the observation of the shift in resonant frequency.

Glaucoma is an eye disease, which may damage the optic nerves and leads to vision loss. Even though it might be caused by different factors, in most of the patients, it is caused by the increase of intraocular pressure and might eventually cause irreversible blindness. Today, there are several different methods to detect the symptoms of glaucoma, such as measuring central corneal thickness, measuring peripheral vision, examining the optic nerve and measuring the eyeball pressure ("Five Common Glaucoma Tests", glaucoma.org, Glaucoma Research Foundation, Apr. 22, 2013). It was demonstrated that the radius of curvature of the sclera is well correlated with the intraocular pressure, while the radius of the curvature of the cornea is insensitive to the changes in intraocular pressure (B. K. Pierscionek, M. Asejczyk-Widlicka, R. A. Schachar, "The effect of changing incraocular pressure on the corneal and scleral curvatures in the fresh porcine eye", Br J. Ophthalmol 2007; 91:801-803. doi: 10.1136/bjo.2006.110221). Noninvasive monitoring of the intraocular pressure has been demonstrated using piezoresistive (M. Leonardi, P. Leuenberger, D. Bertrand, A. Bertsch, P. Renaud, "First Steps toward Noninvasive intraocular Pressure Monitoring with a Sensing Contact Lens", Invest. Ophthalmol. Vis. Sci., 45(9), 3113 (2004)) and capacitive (D. Piso, P. Veiga-Crespo, E. Vecino, "Modern Monitoring Intraocular Pressure Sensing Devices Based on Application Specific Integrated Circuits", Journal of Biomaterials and Nanobiotechnology, 2012, 3, 301-309) sensors embedded on soft contact lenses. It is possible to monitor the progress of the disease in noninvasive and continuous manner using this approach. However, these sensors are electrically active and require application of electrical signals in the contact lens during operation. In addition, the system on the contact lens also includes a transmission circuitry to send the signals to an external unit.

Conventional methods of glaucoma detection using contact lenses employ electrically active sensors and readout electronics embedded with the lenses (M. Leonardi, P. Leuenberger, D. Bertrand, A. Bertsch, P. Renaud, "First Steps toward Noninvasive Intraocular Pressure Monitoring with a Sensing Contact Lens", Invest. Ophthalmol. Vis. Sci., 45(9), 3113 (2004)). The sensors should be powered up electrically to operate and the processed data should be transferred using wireless RF links. This poses a significant limitation for the systems to be integrated on contact lenses that are in continuous contact with eye. First, it is not desirable to have electrically active circuits in contact with eye. Secondly, the power requirement for these systems can be demanding. In addition, both packaging and the implementation of the sensor with integrated readout electronics are expensive for a disposable sensor.

SUMMARY

The purpose of this invention is to provide a sensor which is electrically passive, wireless and low cost to measure intraocular pressure. The sensor on the lens does not require any electrical signal to operate and are interrogated by external antennas that can be located away from the contact lens. We use silver conductive paint to define the rings on flexible substrates. This is very advantageous to define flexible strain sensors that are required for applications as glaucoma detection.

DETAILED DESCRIPTION OF THE INVENTION

Hereinafter this invention will be further described in conjunction with the accompanying figures and embodiments.

The sensor that is a metallic ring can be placed on a contact lens using standard methods of metal deposition (sputtering, evaporation, etc.) using a shadow mask. Alternatively inkjet printing for metals can be used. The sensors can be encapsulated inside the polymeric structure of the contact lens using lamination.

The ring is placed on a contact lens that conforms the surface of the eye. A change in intraocular pressure results in a change in radius of curvature of the ring. For example, an increase in pressure increases the radius of curvature. Likewise, a decrease in pressure decreases the radius of curvature. Thus, the effective capacitance and inductance of the ring changes result in a change in the resonant frequency. The equations are valid for the calculation of the nominal resonant frequency of the ring and give an overall understanding of the resonant frequency.

Split-ring resonators (SRRs) behave like RLC circuits but in most cases the material is chosen so that the resistance value is negligible. Hence the structure might be reduced to LC resonator and the value of resonant frequency might be calculated by Equation 1.

$$f_o = \frac{1}{2\Pi\sqrt{LC}} \quad (1)$$

The inductance of the ring is expressed in equation 2 as a function of geometrical parameters.

$$L = \mu_0 R_m \left( \log \frac{8R_m}{h+w} - \frac{1}{2} \right) \quad (2)$$

where $\mu_0$ is the free-space permeability, $R_m$ is the effective radius of the ring, w and h are the width and the height of the ring, respectively.

The capacitance of the ring has two components, the gap capacitance and surface capacitance. The gap capacitance is calculated as follows:

$$C_{gap} = \varepsilon_0 \frac{hw}{g} + C_0 \quad (3)$$

where $\varepsilon_0$ is the free-space permittivity. $C_0$ is the capacitance caused by the fringing fields and can be calculated as $C_0 = \varepsilon_0$ (h+w+g). Equation 3 assumes that the ring is in free-space. If the ring is placed on or embedded into a dielectric substrate, then the effective permittivity of the medium should be considered in this equation.

The resonant frequency of the ring is used as the sensing parameter. Changes in structural parameters affect the capacitance of the sensor more than its inductance. An increase in gap (g in Equation 3) results in an increase in capacitance. That results in a decrease in resonant frequency (equation 1). On the other hand, increases in width (w) and height (h) of the sensor result in an increase in capacitance, so a decrease in resonant frequency.

The geometry of the SRR structure is determined so that it can be placed around the boundary between cornea and sclera where the change in intraocular pressure can be measured effectively to diagnose glaucoma. In addition, the sensor is optimized for S-band (2-4 GHz) of the electromagnetic band.

Figure 1A:
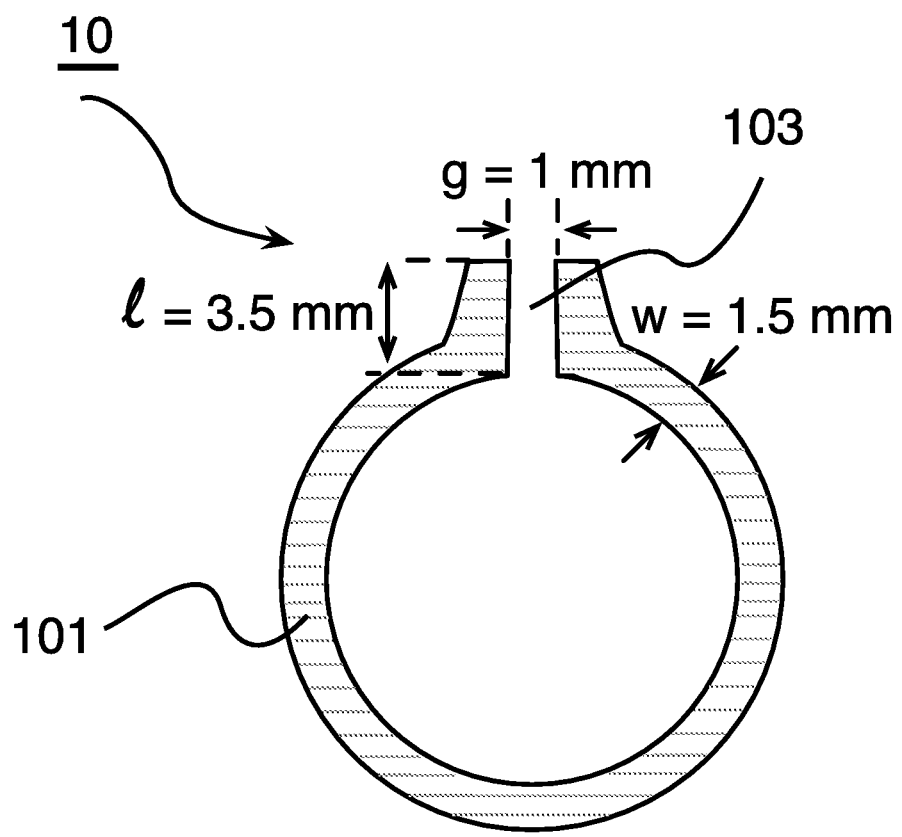
FIG. 1A shows the front view of a sensor of one embodiment of the invention.

FIG. 1A shows a photograph of sensor 10 placed on a flexible substrate made of cellulose acetate. Gap region 103 may be extended to increase the gap capacitance and to keep the resonant frequency of the device in S-band. We applied silver conductive paint (SCP, Electrolube, United Kingdom) to define the ring using a hard mask on the substrate. The thickness of ring 101 is 500 μm and the other relevant geometrical parameters are shown in FIG. 1A. For example, the width of ring 101 is 1.5 mm. The width of gap region 103 is 1 mm. The gap extension L is 3.5 mm. We prepared another type of sensor on a spherically deformed substrate made of latex rubber with a thickness of 50 μm. Using a hard mask on a spherical substrate is not possible, so we painted the ring on the second substrate.

In a preferred embodiment, the painted or the printed ring is embedded in a contact lens. The sensor layer is laminated inside the polymeric structure of the contact lens. As described above, an increase in intraocular pressure results in an increase in radius of curvature of the contact lens that conforms the eyeball. Thus, painted (or the printed) ring on the surface of the contact lens expands. This results in changes in the geometry of the deformed ring. The resonant frequency of the ring is determined by the geometrical parameters of the ring, so the resonant frequency changes as a result of a change in intraocular pressure.

Figure 1B:
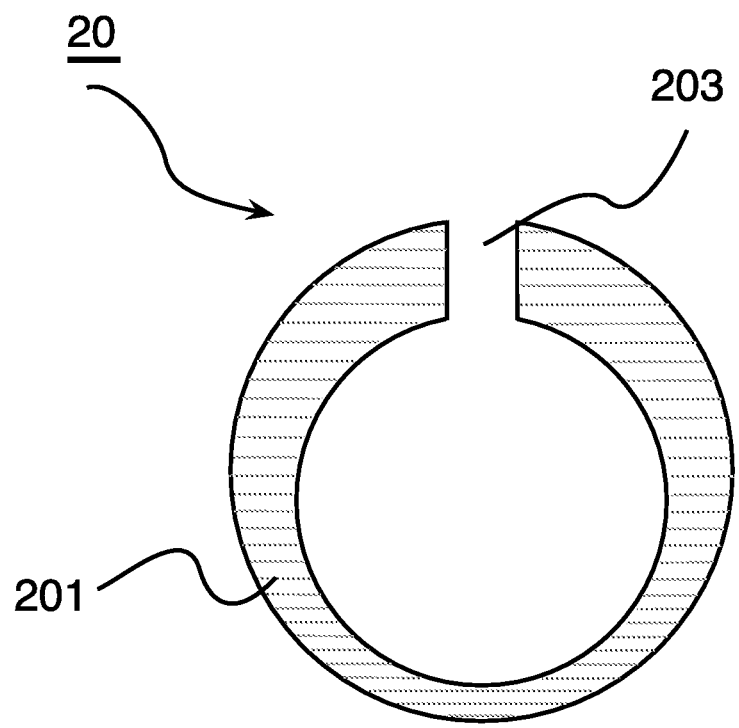
FIG. 1B shows the front view of a sensor of another embodiment of the invention.

FIG. 1B shows another design of sensor 20 with similar geometrical parameters as that shown in FIG. 1A. As shown in FIG. 1B, sensor 20 may include ring 201 and gap region 203. The principles of the sensor 20 are similar with those of sensor 10 as shown in FIG. 1A. Thus, they are not repeated hereinafter.

We simulated the device using commercially available electromagnetic simulation software (CST Microwave Studio, Darmstadt, Germany) to obtain its scattering parameters. We performed the simulations in time domain.

Figure 1C:
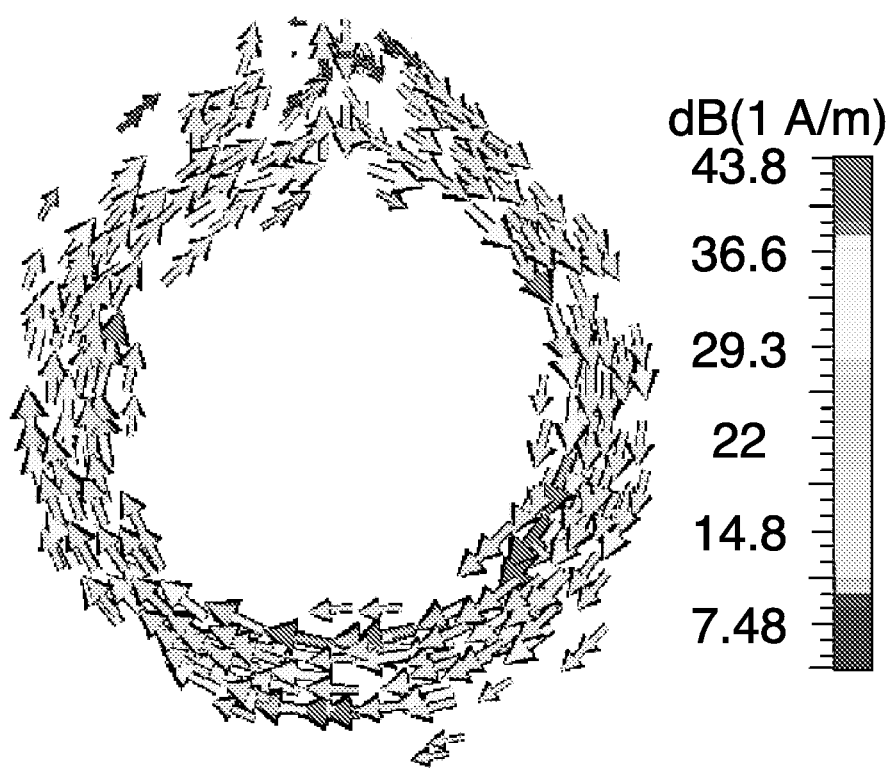
FIG. 1C shows the simulated distribution of surface current density for the device at resonance.

FIG. 1C shows the surface current density along the conductor path at the resonant frequency observed at 2.54 GHz. The magnetic field is perpendicular to the surface of the device for the simulation that supports the circulating current at resonance.

Observation of circular pattern in current density indicates that the resonance is due to magnetic field coupled to the resonator. The colors in FIG. 1C indicate the strength of current density. The legend shows the observed values of current density. The change in radius of curvature of the resonator due to intraocular pressure alters the current density.

Figure 1D:
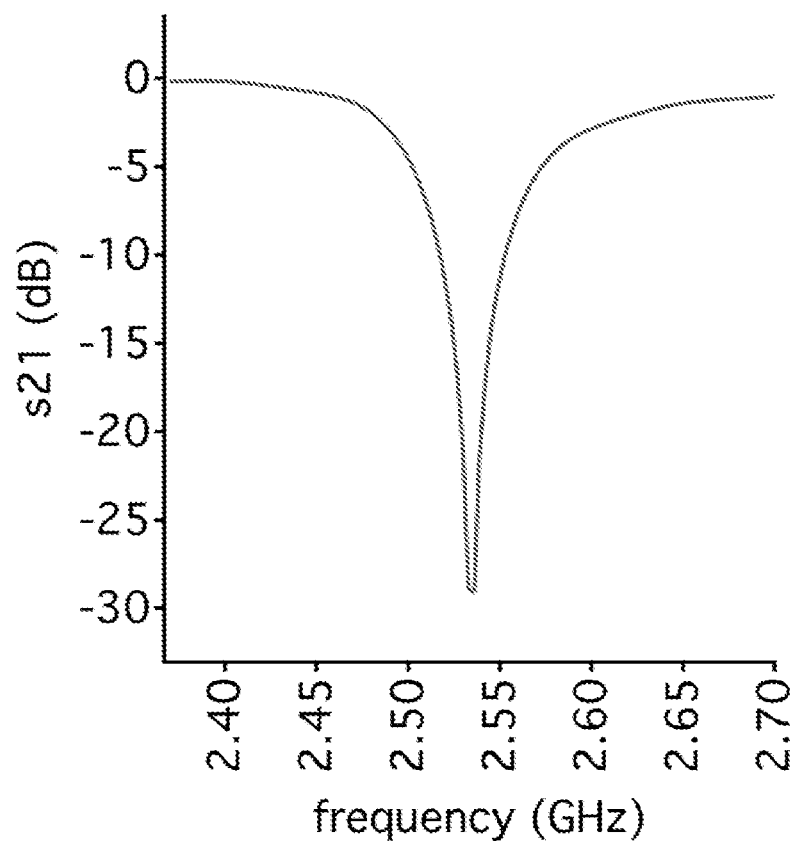
FIG. 1D shows the simulated s21 spectrum of the device.

FIG. 1D shows the s21 spectrum of the device with these settings. As shown in FIG. 1D, s21 spectrum of the measurement exhibit a sharp dip at the resonant frequency of the sensor. Any change in resonant frequency of the ring due to the changes in intraocular pressure results in a shift in the location of the dip. This change can be measured using the antenna pair by obtaining the scattering parameters.

We used the second setup to characterize the SRR sensor realized on the substrate of latex rubber.

Figure 2A:
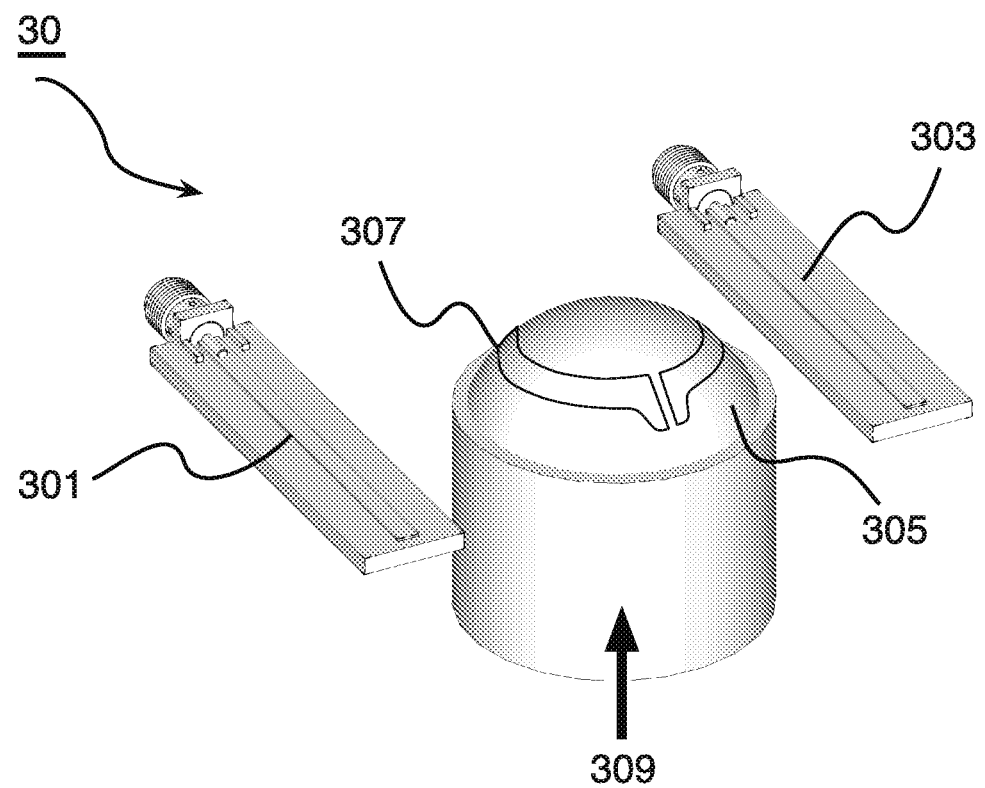
FIG. 2A shows the three-dimensional drawing of the experimental setup for the SRR sensor realized on latex rubber.

FIG. 2A shows the experimental setup where substrate 305 is stretched on top of a cylindrical injection syringe with a diameter of 9 mm. The syringe is used to pump air in and out of the device. First, the air is pumped through air port 309 so that the radius of the curvature of substrate 305 becomes 13 mm. Then, the SRR structure is painted on the surface and its s21 spectrum is obtained using the vector network analyzer. Following measurements by evacuating 0.2 ml air at each step is performed, obtaining the s21 spectrum of the device. The inflated device shrinks with decreasing air volume so does the radius of the curvature.

As shown in FIG. 2A, the resonant frequency of ring 307 is measured using an antenna pair (301, 303) that transmit and receive electromagnetic radiation at the frequency of the resonator. The antenna pair can be placed within the vicinity of the contact lens (not shown). In a preferred embodiment, the antenna pair is placed on eyeglasses (not shown). The contact lens (not shown) is located between the transmitter antenna and the receiver antenna. The scattering parameters are measured between the antennas 301 and 303.

There are two antennas 301 and 303 in the pair. Transmitting antenna 301 is serve as a transmitter, and receiving antenna 303 is the receiver.

The transmitted signal passes through ring 307 of the the passive sensor. The sensor characteristics alter the signal passing through itself.

The antennas are the ports for the measurement circuit (not shown). A fundamental measurement technique is implemented to measure scattering parameters (s-parameters) between the ports S-parameters are commonly used to measure electrical characteristics between the ports at radio frequencies (RF). A vector network analyzer is used to measure the electrical characteristics. A power signal is applied to the transmitting antenna 301 (port-1) and the frequency of the applied power signal is swept using a synthesized sweeper. The applied signal is converted to a propagating electromagnetic wave at the transmitting antenna 301. The receiving antenna 303 (port-2) captures the propagated electromagnetic wave and the wave is converted an electrical signal at port-2 (receiving antenna 303). S21 spectrum is obtained by comparing the amplitude of the phase of the received signal at port-2 (receiving antenna 303) with respect to the input voltage applied to port-1 (transmitting antenna 301) at different frequencies. S21 is a measure of the signal coming out port-2 (receiving antenna 303) relative to the RF stimulus entering port-1 (transmitting antenna 301). A vector network analyzer is used for obtaining the s21 spectrum and the signal processor of the network analyzer is used for this purpose. The characteristics of the sensor affect the electromagnetic wave traveling through itself. At the resonance, the sensor structure absorbs the electromagnetic wave that causes a dip in the s21 spectrum.

In a preferred embodiment the readout mechanism includes two identical monopole patch antennas.

In a preferred embodiment the readout circuit for the biosensors is standalone. The circuit eliminates the need for a vector network analyzer. The readout circuit is based on an oscillator circuit that uses the sensor as a resonator. The ports of the antennas are directly connected to the oscillator circuit that oscillates at the resonant frequency of the sensor. The output of the oscillator circuit is a sine wave at the frequency of the sensor. The frequency of the oscillation is altered due to the operation of the sensor and can be measured at the output of the oscillator circuit.

In a preferred embodiment, the antennas can be located on eyeglasses where all the mentioned units can be integrated.

The readout configurations can be various. For example, one readout configuration uses eyeglasses that include the antennas and the interfacing electronics. The measured pressure can be transmitted wirelessly from the eyeglasses to a display unit or a computer or a mobile phone.

Alternatively, another readout configuration is based on the utilization of hardware and software of a mobile phone for readout purposes. In this configuration, the user wears contact lenses and brings a mobile phone next to the contact lenses. The integrated Bluetooth antenna of the mobile phone can be used to interrogate the sensor wirelessly.

Figure 2B:
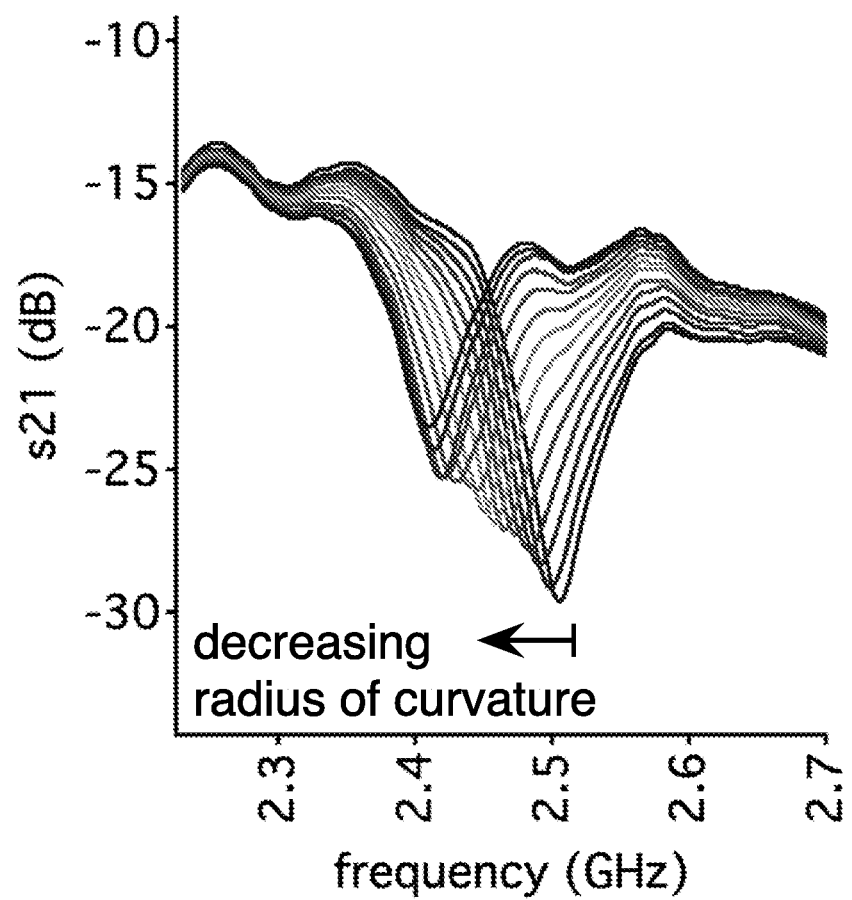
FIG. 2B shows s21 the spectra of the device as the curvature $(1/\rho)$ increases.
Figure 2C:
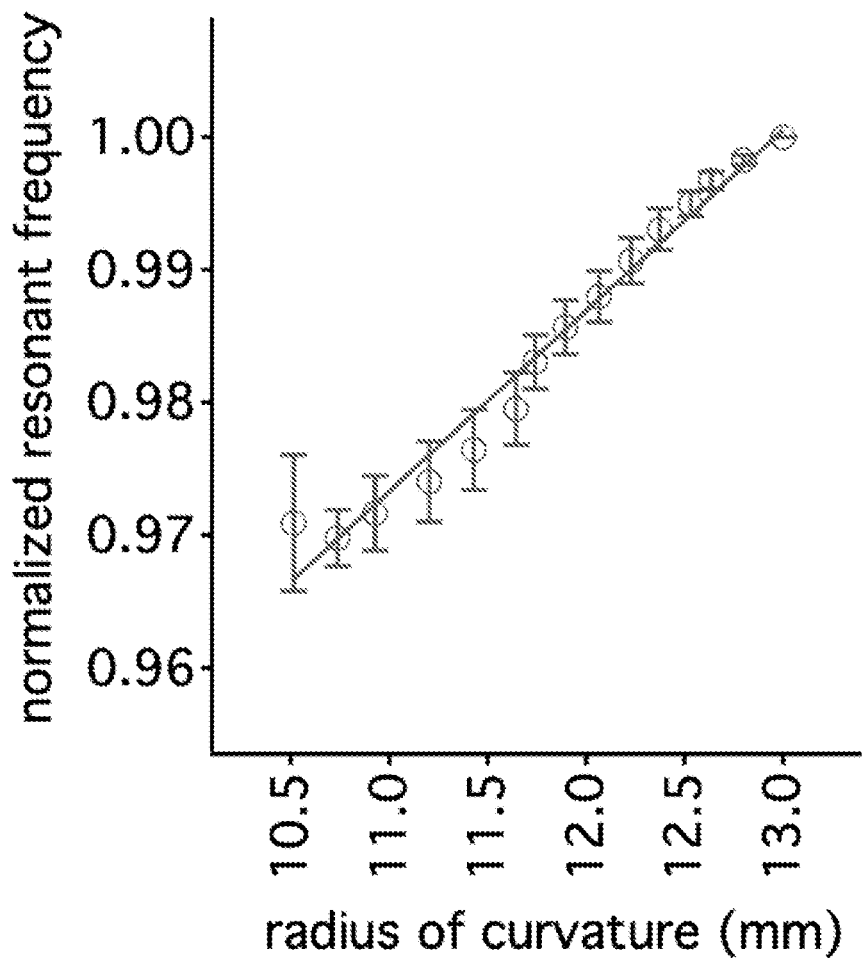
FIG. 2C shows the variation of the resonant frequency as a function of radius of curvature.

FIG. 2B shows how the s21 spectrum of the device changes with decreasing radius of curvature. The measurement sensitivity is based on the quality factor of the resonator and as shown in FIG. 2(b), the quality factor does not change significantly as a function of radius of curvature. The gap of the SRR structure decreases as the radius of the curvature decreases. This results in an increase in the capacitance of the resonator, so the resonant frequency decreases as shown in FIG. 2C. We repeated this experiment six times with different substrates and painted the SRR structure each time separately after we pumped air such that the radius of the curvature became 13 mm.

FIG. 2C shows the mean values and the standard error mean values of the measured resonant frequencies normalized to the value we measured for the radius of curvature of 13 mm. The range of the change in radius of the curvature is physiologically relevant to the diagnosis of glaucoma. The result of an experiment conducted with 16 fresh porcine eyes, by applying five consecutive incremental 100 µl injections, suggests that with each incremental injection of fluid, intraocular pressure and radius of curvature of the sclera increases linearly from 9 mm to 13 mm.

An increase in radius of curvature (as a result of a change in intraocular pressure) means the painted (or the printed) ring on the surface of a contact lens will have a larger surface area while preserving its volume. So, its width and gap will increase while its height decreases. In addition, the deformed shape alters the operation of the device and introduces additional effects that are not expressed in above Equations 1-3. So, it is important to experimentally characterize the sensor within the radii of curvature of interest. FIG. 2(c) indicates the resonant frequency increases with increasing radius of curvature within the probed range. The sensitivity is based on the quality factor of the resonator and as shown in FIG. 2(b), the quality factor does not change significantly as a function of radius of curvature.

What is claimed is:

1. A biomedical pressure sensor comprising:
   a flexible substrate; and
   a flexible resonator disposed on the flexible substrate, wherein a change in a shape of the flexible resonator changes a resonant frequency of the flexible resonator, and
   wherein the flexible resonator is a split-ring which includes a gap and two extension portions at both ends of the gap.

2. The biomedical pressure sensor according to claim 1, wherein the flexible substrate is made of cellulose acetate.

3. The biomedical pressure sensor according to claim 1, wherein an inductance of the split-ring is expressed by the following equation:

$$L = \mu_0 R_m \left( \log \frac{8R_m}{h+w} - \frac{1}{2} \right)$$

wherein $\mu_0$ is free-space permeability, $R_m$ is effective radius of the split-ring, w is a width of the split-ring, and h is a height of the split-ring;

wherein a capacitance of the gap is calculated as follows:

$$C_{gap} = \varepsilon_0 \frac{hw}{g} + C_0$$

wherein $\varepsilon_0$ is free-space permittivity, $C_0$ is the capacitance caused by fringing fields and can be calculated as $C_0 = \varepsilon_0(h+w+g)$.

4. The biomedical pressure sensor according to claim 1, wherein the split-ring has the resonant frequency in S-band which is 2-4 GHz of an electromagnetic band.

5. The biomedical pressure sensor according to claim 1, wherein the split-ring is made of a silver conductive paint.

6. The biomedical pressure sensor according to claim 1, wherein a thickness of the split-ring is 500 μm.

7. The biomedical pressure sensor according to claim 1, wherein a width of the split-ring is 1.5 mm.

8. The biomedical pressure sensor according to claim 1, wherein a width of the gap is 1 mm.

9. The biomedical pressure sensor according to claim 1, wherein a length of the two extension portions is 3.5 mm.

* * * * *